(12) United States Patent
DiCanio et al.

(10) Patent No.: US 8,489,539 B2
(45) Date of Patent: Jul. 16, 2013

(54) COMPUTER-AIDED DIAGNOSTIC SYSTEMS AND METHODS FOR DETERMINING SKIN COMPOSITIONS BASED ON TRADITIONAL CHINESE MEDICINAL (TCM) PRINCIPLES

(75) Inventors: Denise M. DiCanio, Centereach, NY (US); Arlette Palo, New York, NY (US); Jing Cheng, Shanghai (CN); Rose Marie Sparacio, Manorville, NY (US); Julie A. Hidalgo, West Islip, NY (US); Eric G. Yovine, Bronx, NY (US)

(73) Assignee: ELC management, LLC, New York, NY (US)

( * ) Notice: Subject to any disclaimer, the term of this patent is extended or adjusted under 35 U.S.C. 154(b) by 513 days.

(21) Appl. No.: 12/893,447

(22) Filed: Sep. 29, 2010

(65) Prior Publication Data
US 2011/0238604 A1    Sep. 29, 2011

Related U.S. Application Data

(60) Provisional application No. 61/248,503, filed on Oct. 5, 2009.

(51) Int. Cl.
*G06F 17/00* (2006.01)
*G06N 5/04* (2006.01)

(52) U.S. Cl.
USPC .............................................. 706/60

(58) Field of Classification Search
USPC .............................................. 706/60
See application file for complete search history.

(56) References Cited

U.S. PATENT DOCUMENTS

| | | | |
|---|---|---|---|
| 2002/0098590 A1* | 7/2002 | Hsu ................ | 436/86 |
| 2002/0194022 A1* | 12/2002 | Comite .............. | 705/2 |
| 2003/0207280 A1* | 11/2003 | Hsiao et al. ........ | 435/6 |
| 2004/0078221 A1* | 4/2004 | Chen et al. ......... | 705/2 |
| 2005/0123629 A1* | 6/2005 | Chan et al. ........ | 424/728 |
| 2008/0139966 A1* | 6/2008 | Zhang et al. ........ | 600/590 |
| 2010/0022895 A1* | 1/2010 | Kim et al. ........... | 600/485 |
| 2010/0233301 A1* | 9/2010 | Cheng et al. ....... | 424/728 |
| 2010/0235183 A1* | 9/2010 | Firminger et al. .... | 705/2 |
| 2010/0280350 A1* | 11/2010 | Zhang ............... | 707/802 |
| 2011/0304718 A1* | 12/2011 | Pan et al. .......... | 348/77 |
| 2012/0124051 A1* | 5/2012 | Lin et al. ........... | 707/739 |
| 2012/0283573 A1* | 11/2012 | Gong et al. ......... | 600/476 |

FOREIGN PATENT DOCUMENTS

| | | |
|---|---|---|
| JP | 20022024637 | 1/2002 |
| KR | 20010016035 | 3/2001 |
| KR | 100743158 | 7/2007 |

OTHER PUBLICATIONS

Ahn, N.-H. and Ha, J.-I. "System and its method for providing remedy of skin care and obesity care by diagnosing one's physical constitution". Machine Translation to English of KR10-0743158, which was Published Jul. 27, 2007.*
Wang, X. et al. "A self-learning expert system for diagnosis in traditional Chinese medicine." Expert systems with applications, vol. 26, No. 4. 2004. pp. 557-566.*
Huang, M.-J. et al. "Integrated design of the intelligent web-based Chinese Medical Diagnostic System (CMDS)—Systematic development for digestive health". Expert Systems With Applications, vol. 32, issue 2. Elsevier Science. Feb. 2007. pp. 658-673. ISSN: 0957-4174 DOI: 10.1016/j.eswa.2006.01.037.*
PCT International Search Report; International Application No. PCT/US2010/050909; Completion Date: May 16, 2011; Date of Mailing: May 18, 2011.
PCT Written Opinion of the International Searching Authority; International Application No. PCT/US2010/050909; Completion Date: May 16, 2011; Date of Mailing: May 18, 2011.

* cited by examiner

*Primary Examiner* — Jeffrey A Gaffin
*Assistant Examiner* — Benjamin Buss
(74) *Attorney, Agent, or Firm* — Yongzhi (Mimi) Yang; Cynthia R. Miller

(57) ABSTRACT

Computer-aided systems and methods are provided for determining the skin composition of a specific user according to Traditional Chinese Medicinal (TCM) principles by statistically analyzing biological and/or psychological information collected from such user, such as age, gender, bodily sensation, skin condition and complexion, sleep pattern, dietary habits, energy level, stress level, physical fitness and emotional wellness, so as to classify the skin composition of the user according to TCM principles but without employing a TCM practitioner. Preferably, the skin composition classification is indicative of Yin-Yang balance of the skin of the user or the lack thereof. The present systems and methods may further recommend to the user one or more topical skin care regimens and/or ingestible skin benefit products suitable for the skin composition of the specific user.

34 Claims, No Drawings

COMPUTER-AIDED DIAGNOSTIC SYSTEMS AND METHODS FOR DETERMINING SKIN COMPOSITIONS BASED ON TRADITIONAL CHINESE MEDICINAL (TCM) PRINCIPLES

CROSS-REFERENCE TO RELATED APPLICATIONS

This application claims priority from U.S. Provisional Patent Application No. 61/248,503, filed Oct. 5, 2009.

FIELD OF THE INVENTION

The present invention relates to computer-aided diagnostic systems and methods for determining the skin composition of a specific user according to Traditional Chinese Medicinal (TCM) principles.

BACKGROUND OF THE INVENTION

There is great interest in the cosmetic industry to develop products containing natural plant-derived materials that may be applied topically to the skin to provide anti-acne, anti-oil, and anti-cellulite benefits. Plant-based cosmetic products that enhance the appearance of skin are increasingly in demand. Active ingredients or components with skin care benefits can be obtained from either the entire plant or various parts of a plant, such as seeds, needles, leaves, roots, bark, cones, stems, rhizomes, callus cells, protoplasts, organs and organ systems, and meristems, either as dried powders or liquid extracts, which can then be incorporated into topical compositions.

Traditional Chinese Medicine (hereinafter "TCM") has been in existence for several thousands of years and is based largely on accumulated human experience in using naturally occurring plant and animal extracts to treat various diseases. In recently years, TCM practices have gained significant recognition by the Western world, especially for treatment of chronic pathological conditions. Certain TCM ingredients have been known to have skin care benefits for thousands of years, and cosmetic or skin care products containing such TCM ingredients are becoming more popular. Because the TCM ingredients are all natural, they are significantly more appealing to customers who are conscious of the side effects and adverse environmental impacts of synthetic compounds.

However, it is important to note that the basic principles of TCM are quite different from that of the western medicinal sciences. For example, TCM takes a holistic view of the human bodies and believes that an internal physiological balance has to be maintained for a person to be healthy, and all diseases are caused by one or more types of imbalances, and each type of imbalances manifests through an identifiable pattern of symptom and requires a particular set of treatments for correction. Typically, a TCM practitioner first exams an individual patient through various non-invasive techniques, including observing certain physiological characteristics of such patient, listening to the patient's voices, sensing any change in the patient's bodily odor or temperature, feeling the patient's pulse, asking various questions about the history and development of the disease, and gathering any other information that may be related to the patient's health condition, before rendering an opinion on the specific type of imbalance or disease the patient is suffering. Then the TCM practitioner will prescribe a blend of multiple herbal ingredients for treating various symptoms of the disease and helping to re-establish the internal physiological balance of the patient. In other words, the TCM practice takes an individualized treatment approach, instead of a "one-size-fits-all" approach.

The currently available skin care products containing naturally occurring TCM ingredients are mass-marketed to all consumers and fail to implement the individualized treatment approach of TCM. Therefore, it would be desirable to provide new cosmetic and skin care products containing TCM ingredients that adopt the individualized treatment approach of TCM in improving the appearance and skin condition of specific users.

However, a major challenge for implementing the individualized treatment approach of TCM is that a correct diagnosis requires proper application of very complicated TCM principles, which were established through trial-and-error over thousands of years and which are still not well understood by the Western world to this date. Only very experienced TCM practitioners can master such an art of diagnosis, but it is cost-prohibitive to employ a TCM practitioner at each retail location for diagnosing patients and recommending skin care products appropriate for the individual patients.

Therefore, it is an object of the present invention to provide computer-aided diagnostic systems and methods for rapidly and accurately determining the skin compositions of a specific user according to TCM principles and optionally for recommending skin care products suitable for the skin composition of the specific user, but without having to employ a TCM practitioner at each retail location.

SUMMARY OF THE INVENTION

The present invention in one aspect relates to a computer-aided diagnostic system for determining the skin composition of a specific user according to Traditional Chinese Medicinal (TCM) principles, said system comprising:

(1) a data entry module configured for entering into the system a clinical data set obtained from the specific user, wherein the clinical data set contains biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user;

(2) a data processing module in communication with the data entry module, wherein the data processing module is configured for applying a statistical classification process to the clinical data set so as to classify the skin composition of the specific user according to TCM principles; and (3) an output module in communication with the data processing module and configured for displaying the skin composition of the specific user as determined by the data processing module.

Preferably, the skin composition classification of the specific user is indicative of Yin-Yang balance of the skin of the specific user or the lack thereof. The data processing module may be further configured for recommending one or more topical skin care regiments and/or ingestible skin benefit products for the skin composition of the specific user.

In another aspect, the present invention is related to a computer-readable medium comprising code for determining the skin composition of a specific user according to Traditional Chinese Medicinal (TCM) principles, such code comprising instruction for applying a statistical classification process to a clinical data set obtained from the specific user so as to classify the skin composition of the specific user according to TCM principles, wherein the clinical data set comprises biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user.

In yet another aspect, the present invention is related to a method for determining the skin composition of a specific user according to Traditional Chinese Medicinal (TCM) principles, comprising:

(1) obtaining a clinical data set from the specific user, which comprises biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user;

(2) applying a statistical classification process to said clinical data set of the specific user for classifying the skin composition of the specific user according to TCM principles; and (3) outputting the skin composition of the specific user so determined.

The above-mentioned biological and/or psychological information of the user can be collected through different sources. For example, at least some of the biological and/or psychological information in the clinic data set is obtained through the specific user's self-evaluation as prompted by a questionnaire containing various questions related to one or more topics selected from the group consisting of age, gender, bodily sensation, skin condition and complexion, sleep pattern, dietary habits, energy level, stress level, physical fitness, and emotional wellness of the user. Such self-evaluation can be conducted either remotely by allowing the user to fill out the questionnaire online, or on site at a retail location. Some of the biological and/or psychological information can also be obtained through evaluation of the specific user by a trained holistic beauty specialist, and such evaluation can be conducted either remotely through interactive consultation via the internet or on site at a retail location. Further, some of the biological and/or psychological information can be obtained through measurements conducted on the specific user by an electronic device.

The statistical classification process as employed by the present invention may employ any suitable classification technique, such as discriminant analysis, logistic regression, naive Bayes classifier, support vector machines, quadratic classifiers, neural networks, perceptrons, decision trees, Bayesian networks, hidden Markov models, and combinations thereof. The statistical classification process may comprise multiple classification functions, each of which is associated with a specific skin composition and is used to compute a classification score for a user representing the likelihood of the user being classified by a TCM practitioner as having the specific skin composition associated with the respective classification function, wherein the skin composition associated with the classification function that renders the highest classification score for the user is classified as the skin composition of the user. The classification functions can be either linear or quadratic functions.

In a preferred, but not necessary, embodiment of the present invention, the classification functions are constructed by a discriminant analysis comprising:

(a) obtaining a training data set that comprises biological and/or psychological information of multiple users in a training sample selected from a population and classification of such users by a TCM practitioner with respect to their skin compositions according to TCM principles;

(b) identify a group of independent variables, each of which is representative of one type of biological and/or psychological information of the users in the training sample;

(c) calculating an F ratio for each one of the group of independent variables, which is indicative of the capability of the independent variable in discriminating between different groups of users of different skin compositions as determined by the TCM practitioner, wherein the F ratio for a specific independent variable is calculated as the ratio of between-group variance of such independent variable over the average within-group variance of such independent variable;

(d) selecting the independent variable with the largest F ratio;

(e) calculating F ratios for the remaining independent variables;

(f) repeating steps (d)-(e) until all independent variables having F ratios greater than a pre-set level of significance have been selected; and (g) using the selected independent variables to construct the multiple classification functions.

In a more preferred embodiment of the present invention, each of the classification functions is a linear function having a general formula $C_x + W_{x1} \times V_1 + W_{x2} \times V_2 + \ldots + W_{xm} \times V_m$, wherein $C_x$ is a constant associated with a specific skin composition $V_1$ to $V_m$ are the selected independent variables, $W_{x1}$ to $W_{xm}$ are coefficients, each of which corresponds with one of the selected independent variables for the skin composition, and each of which is indicative of the relative weights of the selected variables in computing the classification score using the respective classification function.

Other aspects and objectives of the present invention will become more apparent from the ensuring description, examples, and claims.

DETAILED DESCRIPTION OF THE INVENTION, AND PREFERRED EMBODIMENT THEREOF

Introduction

In TCM practices, health is represented as a balance of Yin and Yang, which are opposing forces interconnected and interdependent in the natural world, giving rise to each other in turn. These two forces represent the bipolar manifestation of all things in nature, and because of this, one must be present to allow the other to exist. A constantly changing balance between Yin and Yang should be maintained within the body of a person. When one force is regularly dominating over the other, the health of the patient can become compromised, resulting in illness and disease. Therefore, when diagnosing a patient, TCM practitioners usually try to first determine the exact nature of the Yin/Yang imbalance, and then correct it through the use of acupuncture, herbal remedies, exercise, diet and lifestyle. Once the balance is restored in the body, so is health.

Therefore, according to the TCM principles, the skin composition of a patient can be classified according to the Yin-Yang balance or imbalance in the skin of such user. For example, the skin composition of the user may be classified into one of three categories, including Yang-dominant, balanced, and Yin-dominant. For another example, the skin composition of the user may be classified into one of five different classifications, including Yang-dominant, balanced-to-Yang, balanced, balanced-to-Yin, and Yin-dominant.

An experienced TCM practitioner typically determines the Yin-Yang balance or imbalance of a patient by observing various physiological characteristics of such patient, such as tongue color, tongue fur color, lip color, skin condition and complexion, and the like. Further, the TCM practitioner asks various questions regarding the patient's bodily sensation, sleep pattern, dietary habits, energy level, stress level, physical fitness and emotional wellness, the answers to which may further assist the TCM practitioner in determining the exact type of Yin-Yang balance or imbalance that the patient is experiencing. The TCM practitioner may also listen to the patience's voices, sensing any change in the patient's bodily odor or temperature, feeling the patient's pulse, and gather any other information related to the patient's health condition through non-invasive techniques, which will be taken into consideration for diagnosis.

For example, the balanced skin composition is typically characterized by smooth, radiant, soft and delicate skin with good elasticity and even skin tone, and patients with the balanced skin composition usually also have lips and tongue of light red color with thin, pale white tongue fur color. The Yang-dominant skin composition is typically characterized by reddish cheek and red skin tone, oily skin surface, and tendency to develop allergy, acne, pigmentation, and pre-mature wrinkles. Patients with the Yang-dominant skin composition may also have lips and tongue of bright red color with yellow tongue fur color, and they typically prefer cold drinks, become thirsty very easily, have bitter tastes in the mouth, often sweat when sleeping at night, easily irascible, and often suffer from internal heat. In contrast, the Yin-dominant skin composition is typically characterized by pale skin tone, dry and easily desquamated skin with low water absorption and water retention capacity, and tendency to develop pigmentation and pre-mature wrinkles. Patients with the Yin-dominant skin composition may have pale or blue lips, light red or pale tongue color with white tongue fur color, and they typically prefer hot drinks, have relatively cold hands and feet, are sensitive to temperature decrease, and often feel tired or sleepy.

Determination of the Yin-Yang balance or imbalance of a user according to TCM principles is a very complex task, and only experienced TCM practitioners can make an accurate and speedy diagnosis. Therefore, it presents a challenge for the cosmetic industry to provide TCM-based cosmetic and skin care products for specific users based on his/her particular skin composition to help either maintaining or restoring the Yin-Yang balance in his/her skin.

The present invention is based, in part, upon the surprising discovery that a computer-aided system and method can be used to statistically model diagnoses rendered by an experienced TCM practitioners for a group of users from a training sample with respect to their skin compositions, based on certain biological and/or psychological information learned of such users, and subsequently to predict or classify the unknown skin composition of a user based on biological and/or psychological information learned of such user. In some aspects, the present invention uses statistical algorithms to classify a user's skin composition into a particular category according to TCM principles. In other aspects, the present invention uses statistical algorithms for ruling out the possibility that a user's skin composition belongs to a particular category to aid in the classification of the user's skin composition into a different category.

Definitions

As used herein, the following terms have the meanings as ascribed to them as follows:

The term "classifying" includes "to predict" or "to categorize" a sample with a skin composition. In certain instances, "classifying" is based on statistical evidence, empirical evidence, or both. In certain embodiments, the systems and methods of the present invention use a so-called training sample with known skin compositions as diagnosed by an experienced TCM practitioner according to TCM principles, and collect certain biological and/or psychological information that may be used by the TCM practitioner in rendering the diagnoses from the training sample. Once established, the training data set serves as a basis, model, or template against which the biological information of a user with unknown skin composition is compared, in order to predict into which category the user's skin composition is most likely to be classified by the TCM practitioner according to TCM principles. In certain instances, classifying a particular user is akin to determine the skin composition of the user. In certain other instances, classifying the user is akin to differentiate the skin composition of the user from another type of skin composition.

The term "skin composition" as used herein refers to various categories of a user's skin based on the Yin-Yang balance or imbalance of such user according to TCM principles. In the two specific embodiments of the present invention, the skin compositions of a population are either classified into three categories, including Yang-dominant, balanced, and Yin-dominant, or five categories, including Yang-dominant, balanced-to-Yang, balanced, balanced-to-Yin, and Yin-dominant. However, it is important to note that the actual number of categories is not limited to the specific embodiments illustrated herein.

The term "biological information" as used herein refers to any set of physiological or biological data that represents the distinctive features or characteristics of a user associated with a particular skin composition. For example, the biological and/or psychological information of a user can include age, gender, bodily sensation, tongue color, tongue fur color, lip color, skin condition and complexion, sleep pattern, dietary habits, energy level, stress level, physical fitness and emotional wellness of the user.

Description of the Embodiments

The present invention provides systems and methods for accurately classifying the skin composition of a user according to TCM principles. The present invention implements a statistical classification process to predict the skin compositions of new users according to TCM principles, but without employing a TCM practitioner. The statistical classification process of the present invention may be based on one or more widely used classification techniques, and it uses data collected from certain users in a training sample with known skin compositions (i.e., as diagnosed by an experienced TCM practitioner) to construct one or more classification functions that best correlate the biological and/or psychological information or data of users in the training sample with their skin compositions as diagnosed by the TCM practitioner. Such classification functions can then be used to predict the skin compositions of new users based solely on the biological and/or psychological information or data of such new users, without involving the TCM practitioner.

Biological Information Collection

In order to statistically model the diagnoses of an experienced TCM practitioner, the present invention collects various biological and/or psychological information of the user that may be useful in assisting the TCM practitioner in determining the skin composition of such user. For example, such biological and/or psychological information may include, but is not limited to: age, gender, bodily sensation, tongue color, tongue fur color, lip color, skin condition and complexion, sleep pattern, dietary habits, energy level, stress level, physical fitness and emotional wellness of the user.

At least some of the biological and/or psychological information can be collected by asking the specific user to conduct certain self-evaluation and fill out a questionnaire containing questions related to the above-listed topics. The questionnaire can be completed by the specific user on site at a retain location, or it can be completed remotely online. In some embodiments, the questionnaire comprises a first section containing a set of questions asking the specific user to provide answers regarding certain clinical symptoms typically taken into consideration by a TCM practitioner when examining a patient. For example, the questions may be directed to certain bodily sensations experienced by the specific user, such as feeling of heat at one's palms, tendency of one to sweat (either in general or at certain specific locations, such as hands or feet), tendency of one to feel thirsty and want to drink, tendency of one to feel tired and sleep, tendency of one to suffer from internal heat (which may be manifested as hot flushes or oral ulcers), tendency of one to taste bitter in one's mouth, energy level felt by oneself, and the like. The questions may also be directed to certain observable physiological symptoms of the specific users, such as the color of one's tongue, tongue fur, or lips, the overall skin complexion, and the like. The questionnaire may comprise a second section containing a set of questions asking the specific user to provide answers with more direct relevance to the skin problems suffered by the user. For example, the questions may be directed to skin dryness and/or redness, acne breakouts, pore sizes, unevenness of skin tone, undesirable pigmentation, sebum secretion, existence of lines and wrinkles, sagginess, skin sensitivity, and the like. The questionnaire may comprise a third section containing a set of questions asking the specific user to provide answers relating to his or her life style, such as one's sleep pattern, dietary habits (including smoking, drinking, vitamin intake, caffeine intake, and the like), physical fitness (including exercise frequency and intensity), stress level, emotional wellness, and the like. Optionally, one or more trained holistic beauty specialists may assist the user in filling out certain questions of the questionnaire, such as those related to the tongue color, tongue fur color, lip color, skin complexion, and skin problems of the user. Upon completion of the questionnaire by the user, the answers to the questions can be converted into numerical values for future data processing.

Preferably, but not necessarily, some of the biological and/or psychological information, especially those related to the tongue color, tongue fur color, lip color, skin complexion, and skin problems of the user, may be collected from by a trained holistic beauty specialist, who examines the user and evaluates the particular feature or characteristic of the user according to photo grading scales, so as to improve the objectivity and accuracy of the evaluation. The trained holistic beauty specialist can carry out the user evaluation either on site at a retail location, or remotely through interactive consultation with the specific user via the internet (e.g., by using certain widely available instant messaging application software with video-conferencing capacity, such as iChat or Skype).

Further, some of the biological and/or psychological information may optionally be collected by using an electronic device that takes certain measurements on the specific user. For example, various imaging devices can be used to quantitatively measure coloration of certain parts of the user's body, such as the face, cheeks, lips, tongue, tongue fur, and the like. For another example, various medical devices can be used to quantitatively measure the user's pulse, heart rate, blood pressure, blood glucose level, body fat percentage, energy field, overall blood circulation or local blood circulation, and the like. Some examples of various electronic devices which may be used in collecting information include a Corneometer® CM 825, measuring skin surface hydration; a Sebumeter® SM 815, measuring sebum on the skin surface; a Cutometer®, measuring skin elasticity; a Skin-pH-Meter® PH 905; a Mexameter® MX 18, measuring melanin and/or erythema; a Skin-Thermometer® ST 500, measuring skin temperature; a Tewameter® ST 500; a Colorimeter CL 400, measuring redness; and a Glossymeter GL 490, measuring radiance/dullness, all of which are available from Courage+Khazaka Electronic GmbH, Germany. Such measurement results can then be incorporated into the clinical data set of the user as potential predictors for classifying the skin composition of the user.

Establishment of Training Data Set

In order to establish statistical models for accurately predicting the skin compositions of new users, a training data set must first be obtained, which contains biological and/or psychological information of multiple users from a training sample and the skin compositions of such users as determined by a TCM practitioner according to TCM principles. The training sample is typically selected from the same population from which the new users are to be selected, and the skin compositions of the users in the training sample, since they are already classified by a TCM practitioner according to TCM principles, are therefore deemed as "known." Such training data set provides training models to which statistical classification processes or analyses can be applied in order to formulate either linear or nonlinear classification functions for predicting or classifying the unknown skin composition of a new user based on his or her biological and/or psychological information.

Statistical Classification Analysis

The term "statistical classification process" or "statistical classification analysis" as used herein includes any known classification technique for placing subjects into categories based on knowledge about one or more characteristics or traits inherent in the subjects. The inherent characteristics or traits are typically considered independent variables and referred to as predictors (X), and the category to which the subject is classified is typically considered a dependent variable and referred to as the grouping variable (Y). The goal of statistical classification process or analysis is to predict the group variable Y for a new subject based on a set of predictors X associated with this new subject and a training set of previously grouped subjects. In the present invention, the predictors are the biological and/or psychological information of a user that can be obtained without involvement of a TCM practitioner, and the grouping variable is the skin composition of such user as determined by the TCM practitioner according to TCM principles.

Preferably, but not necessarily, the statistical classification process or analysis of the present invention employs one or more classification techniques selected from the group consisting of discriminant analysis, logistic regression, naive Bayes classifier, support vector machines, quadratic classifiers, neural networks, perceptrons, decision trees, Bayesian networks, hidden Markov models, and combinations thereof. Performance of a specific classification technique depends greatly on the characteristics of the data to be classified. There is no single classification technique that works best on all given problems. Various empirical tests have been performed to compare performance of classification techniques and to find the characteristics of data that optimize the performance of classification techniques. However, determining a suitable classification technique for a given problem is still more of an art than a science to this date.

In the present invention, a discriminant analysis, and more precisely a multi-class linear discriminant analysis, is found to be particularly effective in categorizing the skin compositions of users according to TCM principles. Specifically, the discriminant analysis is carried out by obtaining a training data set as described hereinabove, i.e., which comprises biological and/or psychological information of multiple users in a training sample selected from a population and classification of such users by a TCM practitioner with respect to their skin compositions according to TCM principles. A group of independent variables or predictors (V) is identified, each variable or predictor being representative of one type of biological and/or psychological information of the users in the training sample. An F ratio is calculated for each one of the group of independent variables, which is indicative of the capability of the independent variable in discriminating between different groups of users of different skin compositions as determined by the TCM practitioner. More specifically, the F ratio for a particular independent variable is calculated as the ratio of between-group variance of such independent variable over the average within-group variance of such independent variable. The independent variable with the largest F ratio is initially selected and taken out of the pool of independent variables. The selected independent variable will be included into the classification functions, which are to be constructed once all independent significant discriminating variables between different groups of users are selected. F ratios for the remaining independent variables (the pool excluding the already selected independent variable) are then calculated, and the independent variable with the largest F ratio among these is then selected and taken out of the pool of independent variables. The calculation and selection steps are reiterated until all independent variables having F ratios greater than a pre-set level of significance have been selected.

The selected independent variables are then used to construct classification functions, which can be used to determine which category of skin composition a new user most likely belongs. There are as many classification functions as the number of skin composition categories. Each classification function is associated with a specific skin composition category and can be used to compute a classification score for a new user by entering the biological and/or psychological information of such new user. The classification score outputted by each classification function represents the likelihood of such new user being classified by a TCM practitioner as having the specific skin composition associated with the respective classification function. In other words, for each new user, each classification function will compute a classification score, and the skin composition associated with the classification function that renders the highest classification score is the skin composition of the user.

The classification functions can be either linear or quadratic. In a preferred embodiment of the present invention, the classification functions are linear having a general formula $C_x + W_{x1} \times V_1 + W_{x2} \times V_2 + \ldots + W_{xm} \times V_m$, where $C_x$ is a constant associated with a specific skin composition, $V_1$ to $V_m$ are the selected independent variables, $W_{x1}$ to $W_{xm}$ are coefficients that each correspond with one of the selected independent variables for each skin composition and are indicative of the relative weights of the selected variables in computing the classification score using the respective classification functions. For example, assuming that the skin compositions can be divided into three categories A, B, and C, and that five independent variables $V_1$, $V_2$, $V_3$, $V_4$, and $V_5$ have been selected for constructing the classification functions, there will be three (3) classification functions, each of which is associated with a specific skin composition category. For a specific user with a specific set of values for independent variables $V_1$ through $V_5$, three classification scores $Y_A$, $Y_B$, and $Y_C$ will be calculated as follows:

$$Y_A = C_A + W_{A1} \times V_1 + W_{A2} \times V_2 + W_{A3} \times V_3 + W_{A4} \times V_4 + W_{A5} \times V_5,$$

$$Y_B = C_B + W_{B1} \times V_1 + W_{B2} \times V_2 + W_{B3} \times V_3 + W_{B4} \times V_4 + W_{B5} \times V_5, \text{ and}$$

$$Y_C = C_C + W_{C1} \times V_1 + W_{C2} \times V_2 + W_{C3} \times V_3 + W_{C4} \times V_4 + W_{C5} \times V_5,$$

If $Y_A$ is the largest among all three classification scores computed, it is then concluded that the specific user is most likely to be classified as having skin composition A. However, if $Y_C$ is the largest among all three classification scores computed, it will be concluded that the specific user is most likely to be classified as having skin composition C.

The discriminant analysis as described hereinabove can be readily conducted using widely used statistical computer software programs, such as SPSS, SAS, and the like. Optionally, the classification functions so constructed are further validated using a validation data set, which comprises biological and/or psychological information of multiple users in a validation sample and the skin compositions of such users as determined by a TCM practitioner according to TCM principles. The validation sample is selected from the same population as the training sample, but it contains a different group of users. The prediction made by using the classification functions and the actual skin composition as determined by the TCM practitioner for the users in the validation sample are compared, and a prediction score may be calculated indicative of the percentage of correct prediction made by using the classification functions. If the prediction score is higher than a pre-set threshold, such as, for example 70%, 80%, or 90%, the classification functions are then considered validated and suitable for clinical uses.

The validation sample and the training sample can be selected at the same time. Further, the validation and training phases are not necessarily separated and fixed. The system can be interactive, and the training and validation can be interwoven for fine-tuning the discriminant analysis in order to achieve the best predictions possible.

Computer-Based System

The computer-based system of the present invention may include a computer, which can be either a workstation or a personal computer. Such a computer preferably contains a data entry module, such as a keyboard or a touch-screen, to allow direct entry of users' biological and/or psychological information by the users or by the holistic beauty specialist. The data entry module may also be a direct connection (such as USB, Firewire, or other interface) or a network connection (such as modem or other network connections) for transmitting and receiving use-related biological and/or psychological data, for example, via a portable medium such as a compact disk (CD) or a digital versatile disk (DVD) or via the internet.

The computer further contains a data processing module, such as a central processing unit (CPU), which is in communication with the data entry module. The data processing module is configured for applying the above-described statistical classification process to the user data entered through the data entry module and to thereby classify the skin composition of the specific user according to TCM principles. The data processing module is more specifically under the control of a computer-readable medium containing coded instructions for applying such statistical classification process to the user data.

The computer further contains an output or displaying module in communication with the data processing module for displaying the result determined, i.e., the likely skin composition of the user. Such an output or displaying module may include the computer display screen for visually displaying the result, or a printer for printing the result, or a network connection for outputting the result to a remote location.

Optionally, the computer has a memory module that stores information about various topical skin care regimens and/or ingestible products that are suitable for different skin compositions. Once the skin composition of a particular user is determined by the data processing module, information about skin care regimens and/or ingestible products suitable for the skin composition of such particular user can be retrieved from the memory module and output together with the skin composition determined as skin care recommendations for the user.

In this manner, the present invention can accurately recommend TCM-based skin care products for targeting any sub-population of users (e.g., in any region, country, city, etc.) with a specific skin composition according to the TCM principles, but without employing a TCM practitioner at each retail location.

EXAMPLE 1

A group of 133 Asian female participants between the ages of 22 and 51 was recruited for testing. After registration, each participant was given a questionnaire containing 48 questions covering various aspects of the participant's biological and psychological conditions. For example, the questionnaire may inquire the participant about her age, sensory feel (e.g., fear of cold/heat, sensation of heat at one's palms, palm sweating, sweating pattern, feeling of thirst, feeling of bitterness in one's mouth, suffering from internal heat, and the like), sleep pattern, dietary habits, skin conditions (e.g., skin color/tone, dryness/oiliness, and the like), facial complexion and tones (e.g., redness, darkening, and the like), skin problems (e.g., acne breakouts, pores, uneven skin tone, hyperpigmentation, dark spots, sensitivity, dry patches, lines/wrinkles, sagging, and the like), energy level, stress level, physical and emotional well-being, and the like. An exemplary questionnaire that can be used for practicing the present invention is included herein. It is provided for illustration purposes only, without intending to limit the scope of the present invention in any manner.

TABLE 1

EXEMPLARY QUESTIONNAIRE

| No. | Question | Answers |
|---|---|---|
| 1 | What is your age? | (A) 20~29<br>(B) 30~39<br>(C) 40~49<br>(D) 50~59 |
| 2 | Do you feel cold? | (A) Fear of cold<br>(B) Fear of heat<br>(C) Fear of heat and cold<br>(D) None of the above |
| 3 | Do you have self-hot feeling of your hand palms? | (A) Often<br>(B) Sometimes<br>(C) Seldom<br>(D) Never |
| 4 | Do you easily have hand sweating? | (A) Often<br>(B) Sometimes<br>(C) Seldom<br>(D) Never |
| 5 | Do you easily sweat in the day time? | (A) Often<br>(B) Sometimes<br>(C) Seldom<br>(D) Never |
| 6 | Do you often feel thirsty and want to drink? | (A) Often<br>(B) Sometimes<br>(C) Seldom<br>(D) Never |
| 7 | Do you feel tired and sleepy? | (A) Often<br>(B) Sometimes<br>(C) Seldom<br>(D) Never |
| 8 | How is your sleep quality? | (A) Good<br>(B) Balance<br>(C) Poor (less than 5 hours or a lot of dreams) |
| 9 | What flavors do you prefer? | (A) Heavy flavor (Spicy)<br>(B) Bland flavor<br>(C) No preference |
| 10 | Do you feel bitter in your mouth? | (A) Often<br>(B) Sometimes<br>(C) Seldom<br>(D) Never |
| 11 | Do you have night sweats while you are sleeping? | (A) Often<br>(B) Sometimes<br>(C) Seldom<br>(D) Never |
| 12 | What characteristic best describes you? | (A) Impatient<br>(B) Patient<br>(C) Between (A) and (B) |

TABLE 1-continued

EXEMPLARY QUESTIONNAIRE

| No. | Question | Answers |
|---|---|---|
| 13 | Do you suffer from internal heat (e.g., hot flush, oral ulcers)? | (A) Often<br>(B) Sometimes<br>(C) Seldom<br>(D) Never |
| 14 | How would you describe your facial complexion? | (A) Very Radiant<br>(B) Radiant<br>(C) Somewhat Radiant<br>(D) Dull<br>(E) Very Dull |
| 15 | What is the color of your complexion? | (A) Red<br>(B) Rosy<br>(C) Below Rosy<br>(D) Pale<br>(E) Sallow |
| 16 | What is your skin condition? | (A) Dry skin<br>(B) Normal to dry<br>(C) Normal or balance skin<br>(D) Normal to oil skin<br>(E) Oily skin |
| 17 | What kind of drink do you prefer despite the season? | (A) Cold<br>(B) Hot<br>(C) No preference |
| 18 | Do you have acne breakouts on your face? | (A) Yes<br>(B) No |
| 19 | Do you have large pores on your face? | (A) Yes<br>(B) No |
| 20 | Do you have uneven skin tone? | (A) Yes<br>(B) No |
| 21 | Do you have pigmentation issues on your face? | (A) Yes<br>(B) No |
| 22 | Do you have (facial) dry patches? | (A) Yes<br>(B) No |
| 23 | Do you have severe dry (facial) skin? | (A) Yes<br>(B) No |
| 24 | Do you have facial redness? | (A) Yes<br>(B) No |
| 25 | Do you have more lines/wrinkles than peers? | (A) Yes<br>(B) No |
| 26 | Do you suffer from overall darkening of skin tone, darkening of complexion? | (A) Yes<br>(B) No |
| 27 | Do you have sensitive skin? | (A) Yes<br>(B) No |
| 28 | Do you have dark spot? | (A) Yes<br>(B) No |
| 29 | Do you have more sagging problem than your peers? | (A) Yes<br>(B) No |
| 30 | Do you typically experience any of the following facial skin conditions during the summer and/or winter months?<br>Itch skin<br>Scaling/Flaking<br>Dryness<br>Cracking<br>Excessive oil<br>Acne breakouts<br>None of the above | Please check all that applies to you:<br><br>Summer Months  Winter Months<br>☐  ☐<br>☐  ☐<br>☐  ☐<br>☐  ☐<br>☐  ☐<br>☐  ☐<br>☐  ☐ |
| 31 | Where on your body do you experience acne breakouts, if at all? | (A) Face<br>(B) Neck<br>(C) Chest<br>(D) Back<br>(E) Do not experience acne breakouts |
| 32 | How frequently do you usually experience acne breakouts on your face, if at all? | (A) Once a week or more often<br>(B) About once every two weeks<br>(C) At least once a month<br>(D) Less than once a month<br>(E) Never |
| 33 | How could you rate your physical health compared to others who are your chronological age? | (A) Excellent<br>(B) Very good<br>(C) Good<br>(D) Fair E. Poor |
| 34 | Do you have difficulty falling asleep? | (A) Yes<br>(B) No |

TABLE 1-continued

EXEMPLARY QUESTIONNAIRE

| No. | Question | Answers |
|---|---|---|
| 35 | When you have difficulty staying asleep, for what reasons is your sleep disturbed? | (A) Stress<br>(B) Snoring<br>(C) Physical discomfort<br>(D) Room too warm<br>(E) Noise<br>(F) Light<br>(G) Smells<br>(H) Other: _____<br>(I) Don't know |
| 36 | Are you usually very tired and sleepy upon waking in the morning and want to sleep more? | (A) Yes<br>(B) No |
| 37 | Do you tend to get very sleepy in the evening before bedtime? | (A) Yes<br>(B) No |
| 38 | Do you have seasonal allergies or have fever? | (A) Yes<br>(B) No |
| 39 | What is the severity of your allergies? | (A) Very mild<br>(B) Mild<br>(C) Moderate<br>(D) Severe |
| 40 | How frequently do you take vitamin supplements? | (A) Everyday<br>(B) 5-6 days a week<br>(C) 3-4 days a week<br>(D) 1-2 days a week<br>(E) Less often than once a week<br>(F) Never |
| 41 | How many days a week do you exercise? | (A) Everyday<br>(B) 5-6 days a week<br>(C) 3-4 days a week<br>(D) 1-2 days a week<br>(E) Less often than once a week<br>(F) Never |
| 42 | How often do you skip meals? | (A) Never<br>(B) Sometimes<br>(C) Often<br>(D) Always |
| 43 | Which of the following best describe your typical meal? | (A) Well balanced meal<br>(B) Somewhat balanced meal<br>(C) Not a balanced meal |
| 44 | On average, how many caffeinated drinks do you have everyday? By caffeinated drinks, we mean caffeine energy drinks, coffee, tea and soda. | (A) More than 4 cups/drinks<br>(B) 3-4 cups/drinks<br>(C) Less than 2 cups/drinks<br>(D) None |
| 45 | Thinking about your overall eating habits, how healthy do you eat? | (A) Extremely healthy<br>(B) Very healthy<br>(C) Somewhat healthy<br>(D) A little healthy<br>(E) Not at all healthy |
| 46 | How would you rate your emotional well-being? | (A) Excellent<br>(B) Very good<br>(C) Good<br>(D) Fair<br>(E) Poor |
| 47 | Thinking about your life, in general, how stressful would you say your life is? | (A) Extremely stressful<br>(B) Very stressful<br>(C) Somewhat stressful<br>(D) Slightly stressful<br>(E) Not at all stressful |
| 48 | How well do you feel you deal with stress | (A) Extremely well<br>(B) Very well<br>(C) Somewhat well<br>(D) Slightly well<br>(E) Not at all well |

After filling out the questions on the questionnaire, each participant was directed to a station with a trained skin specialist, who evaluated the following skin conditions of the participant based on a scale of 0 to 10:

(1) Acne breakout;
(2) Pores;
(3) Skin tone;
(4) Age spots;
(5) Redness;
(6) Global facial wrinkles;
(7) Crow's feet;
(8) Moist level;
(9) Elasticity;
(10) Dull-Radiance; and
(11) Skin color variants.

Standard photo scales were developed for the specialist evaluation purposes, based on empirical observations of skin conditions of the Asian sub-population from which the 133 participants were sampled.

After the evaluation by the skin specialist, each participant was directed to a TCM doctor, who asked the participant various questions typical for TCM diagnosis purposes and observed various physiological characteristics of the participant (e.g., pulse, tongue color, tongue fur color, facial complexion, and the like) and then rendered a diagnosis for the participant with respect to the skin composition of such participant according to TCM principles. Specifically, the diagnosis rendered by the TCM doctor categorized each participant into one of five (5) skin composition categories, i.e., Yang-dominant, balanced-to-Yang, balanced, balanced-to-Yin, and Yin-dominant.

The participants were also subject to testing by various devices and instruments, which measured various physiological parameters of the participants, such as skin surface hydration, sebum level, skin elasticity, skin pH value, the amount of melanin contained in the skin cells, erythema, skin temperature, transdermal water-loss (TEWL), skin redness, and radiance-dullness of the skin.

A step-wise, multi-class linear discriminant analysis was then carried out to analyze the testing data as collected hereinabove. Based on the TCM's doctor's diagnosis, the 133 participants were categorized into 5 groups, i.e., Yang-dominant, balanced-to-Yang, balanced, balanced-to-Yin, and Yin-dominant. The answers provided by the participants to the 48 questions on the questionnaire and the 0-10 scaled evaluations of the participants' skin conditions as provided by the trained skin specialist were all treated as independent variables or predictors (V), each of which was representative of one type of biological and/or psychological parameter of the participants for subsequent analysis. The medium/mean values and distributions of the independent variables (V) for each group of participants of a particular skin composition were separately calculated.

An F ratio was then calculated for each one of these independent variables (V) as an indicator of the capability of each particular independent variable (V) in discriminating between different groups of participants of various skin compositions as determined by the TCM practitioner. The independent variable (V) with the largest F ratio was initially selected and taken out of the pool of independent variables (V). F ratios for the remaining independent variables (the pool excluding the already selected independent variable) were then recalculated, and the independent variable with the largest F ratio among these was selected and taken out of the pool of independent variables. The calculation and selection steps were reiterated to select multiple independent variables, which were then used to construct classification functions for determining which category of skin composition a new user most likely belongs. Because there were 5 categories of skin compositions, i.e., Yang-dominant, balanced-to-Yang, balanced, balanced-to-Yin, and Yin-dominant, five (5) different classification functions were constructed, each of which corresponded with a specific skin composition category and each was used to compute a classification score (Y) for a new user by entering the biological and/or psychological information of such new user.

Specifically, the five (5) different classification functions so constructed were as follows:

$$Y_A = C_A + W_{A1} \times V_1 + W_{A2} \times V_2 + W_{A3} \times V_3 + \ldots W_{A52} \times V_{52} + W_{A53} \times V_{53}, \quad (1)$$

$$Y_B = C_B + W_{B1} \times V_1 + W_{B2} \times V_2 + W_{B3} \times V_3 + \ldots W_{B52} \times V_{52} + W_{B52} \times V_{53}, \quad (2)$$

$$Y_C = C_C + W_{C1} \times V_1 + W_{C2} \times V_2 + W_{C3} \times V_3 + \ldots W_{C52} \times V_{52} + W_{C53} \times V_{53}, \quad (3)$$

$$Y_D = C_D + W_{D1} \times V_1 + W_{D2} \times V_2 + W_{D3} \times V_3 + \ldots W_{D52} \times V_{52} + W_{D53} \times V_{53}, \text{ and} \quad (4)$$

$$Y_E = C_E + W_{E1} \times V_1 + W_{E2} \times V_2 + W_{E3} \times V_3 + \ldots W_{E52} \times V_{52} + W_{E53} \times V_{53}, \quad (5)$$

wherein variables $V_1$ through $V_{53}$ are the variables selected through the discriminant analysis (note that there some of the answers corresponding to the respondent questionnaire were broken down into two or more variables, so the total number of variables was larger than that of the questions); wherein $Y_A, Y_B, Y_C, Y_D$ and $Y_E$ are the classification scores calculated for a new user indicative of the likelihood of such user to be categorized as Yin-dominant (hereinafter referred to as "A"), balanced-to-Yin (hereinafter referred to as "B"), balanced (hereinafter referred to as "C"), balanced-to-Yang (hereinafter referred to as "D"), and Yang-dominant (hereinafter referred to as "E") skin composition, respectively; wherein $W_{A1}$ to $W_{A53}$ are coefficients that each correspond with one of the selected independent variables $V_1$ through $V_{53}$ for skin composition A (i.e., Yin-dominant) and are indicative of the relative weights of the selected variables in computing the classification score $Y_A$ for using the first classification function (1) in computing the likelihood of such user to be categorized as having skin composition A (i.e., Yin-dominant); wherein $W_{B1}$ to $W_{B53}$ are coefficients that each correspond with one of the selected independent variables $V_1$ through $V_{53}$ for skin composition B (i.e., balanced-to-Yin) and are indicative of the relative weights of the selected variables in computing the classification score $Y_B$ for using the second classification function (2) in computing the likelihood of such user to be categorized as having skin composition B (i.e., balanced-to-Yin); wherein $W_{C1}$ to $W_{C53}$ are coefficients that each correspond with one of the selected independent variables $V_1$ through $V_{53}$ for skin composition C (i.e., balanced) and are indicative of the relative weights of the selected variables in computing the classification score $Y_C$ for using the third classification function (3) in computing the likelihood of such user to be categorized as having skin composition C (i.e., balanced); wherein $W_{D1}$ to $W_{D53}$ are coefficients that each correspond with one of the selected independent variables $V_1$ through $V_{53}$ for skin composition D (i.e., balanced-to-Yang) and are indicative of the relative weights of the selected variables in computing the classification score $Y_D$ for using the fourth classification function (4) in computing the likelihood of such user to be categorized as having skin composition D (i.e., balanced-to-Yang); wherein $W_{E1}$ to $W_{E53}$ are coefficients that each correspond with one of the selected independent variables $V_1$ through $V_{53}$ for skin composition E (i.e., Yang-dominant) and are indicative of the relative weights of the selected variables in computing the classification score $Y_E$ for using the fifth classification function (5) in computing the likelihood of such user to be categorized as having skin composition E (i.e., Yang-dominant); wherein $C_A, C_B, C_C, C_D$ and $C_E$ are constants each associated with a specific skin composition A, B, C, D, and E, respectively.

The following tables identify each independent variable $V_1$ through $V_{53}$ and the corresponding coefficients and constants associated therewith for each classification function:

TABLE 2

| SELECTED VARIBLES | |
| --- | --- |
| No. | Variables |
| $V_1$ | Specialist-Q1-ACNE BREAKOUT (0 TO 10 SCALE) |
| $V_2$ | Specialist-Q2-PORES (0 TO 10 SCALE) |
| $V_3$ | Specialist-Q3-SKIN TONE (0 TO 10 SCALE) |
| $V_4$ | Specialist-Q5-REDNESS (0 TO 10 SCALE) |
| $V_5$ | Specialist-Q6-GLOBAL FACIAL WRINKLES (0 TO 10 SCALE) |

TABLE 2-continued

SELECTED VARIBLES

| No. | Variables |
|---|---|
| $V_6$ | Specialist-Q8-MOIST LEVEL-MOIST (YES = 1, NO = 0) |
| $V_7$ | Specialist-Q9-ELASTICITY (0 TO 10 SCALE) |
| $V_8$ | Specialist-Q10-DULL-RADIANCE (0 TO 10 SCALE) |
| $V_9$ | Specialist-Q11-SKIN COLOR VARIANTS-ROSY (YES = 1, NO = 0) |
| $V_{10}$ | Respondent-Q2-FEAR OF-COLD (YES = 1, NO = 0) |
| $V_{11}$ | Respondent-Q2-FEAR OF-HEAT (YES = 1, NO = 0) |
| $V_{12}$ | Respondent-Q2-FEAR OF BOTH-HEAT AND COLD (YES = 1, NO = 0) |
| $V_{13}$ | Respondent-Q7-DO YOU FEEL TIRED AND SLEEPY (OFTEN = 4) |
| $V_{14}$ | Respondent-Q12-CHARACTERISTIC DESCRIBING YOU-IMPATIENT (YES = 1, NO = 0) |
| $V_{15}$ | Respondent -Q12-CHARACTERISTIC DESCRIBING YOU-PATIENT (YES = 1, NO = 0) |
| $V_{16}$ | Respondent-Q13-SUFFER FROM INTERNAL HEAT (OFTEN = 4) |
| $V_{17}$ | Respondent-Q14-DESCRIPTION OF FACIAL COMPLEXION-(VERY DULL = 5) |
| $V_{18}$ | Respondent-Q15-COLOR OF COMPLEXION-ROSY (YES = 1, NO = 0) |
| $V_{19}$ | Respondent-Q15-COLOR OF COMPLEXION-SLIGHTLY ROSY (YES = 1, NO = 0) |
| $V_{20}$ | Respondent-Q15-COLOR OF COMPLEXION-PALE (YES = 1, NO = 0) |
| $V_{21}$ | Respondent-Q15-COLOR OF COMPLEXION-SALLOW (YES = 1, NO = 0) |
| $V_{22}$ | Respondent-Q16-SKIN CONDITION-NORMAL TO DRY (YES = 1, NO = 0) |
| $V_{23}$ | Respondent-Q16-SKIN CONDITION-NORMAL OR BALANCED (YES = 1, NO = 0) |
| $V_{24}$ | Respondent-Q16-SKIN CONDITION-NORMAL TO OILY (YES = 1, NO = 0) |
| $V_{25}$ | Respondent-Q18-SKIN PROBLEMS-ACNE BREAKOUTS (YES = 1, NO = 0) |
| $V_{26}$ | Respondent-Q19-SKIN PROBLEMS-LARGE PORES (YES = 1, NO = 0) |
| $V_{27}$ | Respondent-Q24-SKIN PROBLEMS-FACIAL REDNESS (YES = 1, NO = 0) |
| $V_{28}$ | Respondent-Q30-FACIAL SKIN CONDITIONS IN SUMMER-ITCHY SKIN (YES = 1, NO = 0) |
| $V_{29}$ | Respondent-Q30-FACIAL SKIN CONDITIONS IN SUMMER-SCALING/FLAKING (YES = 1, NO = 0) |
| $V_{30}$ | Respondent-Q30-FACIAL SKIN CONDITIONS IN SUMMER-DRYNESS (YES = 1, NO = 0) |
| $V_{31}$ | Respondent-Q30-FACIAL SKIN CONDITIONS IN SUMMER-EXCESSIVE OIL (YES = 1, NO = 0) |
| $V_{32}$ | Respondent-Q30-FACIAL SKIN CONDITIONS IN SUMMER-ACNE BREAKOUTS (YES = 1, NO = 0) |
| $V_{33}$ | Respondent-Q30-FACIAL SKIN CONDITIONS IN WINTER-ITCHY SKIN (YES = 1, NO = 0) |
| $V_{34}$ | Respondent-Q30-FACIAL SKIN CONDITIONS IN WINTER-SCALING/FLAKING (YES = 1, NO = 0) |
| $V_{35}$ | Respondent-Q30-FACIAL SKIN CONDITIONS IN WINTER-DRYNESS (YES = 1, NO = 0) |
| $V_{36}$ | Respondent-Q30-FACIAL SKIN CONDITIONS IN WINTER-EXCESSIVE OIL (YES = 1, NO = 0) |
| $V_{37}$ | Respondent-Q30-FACIAL SKIN CONDITIONS IN WINTER-ACNE BREAKOUTS (YES = 1, NO = 0) |
| $V_{38}$ | Respondent-Q31-WHERE ON BODY EXPERIENCE ACNE BREAKOUT-NECK (YES = 1, NO = 0) |
| $V_{39}$ | Respondent-Q31-WHERE ON BODY EXPERIENCE ACNE BREAKOUT-CHEST (YES = 1, NO = 0) |
| $V_{40}$ | Respondent-Q31-WHERE ON BODY EXPERIENCE ACNE BREAKOUT-BACK (YES = 1, NO = 0) |
| $V_{41}$ | Respondent-Q31-WHERE ON BODY EXPERIENCE ACNE BREAKOUT-DO NOT EXPERIENCE BREAKOUTS (YES = 1, NO = 0) |
| $V_{42}$ | Respondent-Q32-FREQUENCY OF ACNE BREAKOUTS ON FACE (5 = ONCE A WEEK OR MORE) |
| $V_{43}$ | Respondent-Q35-REASONS FOR SLEEP BEING DISTURBED-STRESS (YES = 1, NO = 0) |
| $V_{44}$ | Respondent-Q35-REASONS FOR SLEEP BEING DISTURBED-SNORING (YES = 1, NO = 0) |
| $V_{45}$ | Respondent-Q35-REASONS FOR SLEEP BEING DISTURBED-PHYSICAL DISCOMFORT (YES = 1, NO = 0) |
| $V_{46}$ | Respondent-Q35-REASONS FOR SLEEP BEING DISTURBED-ROOM TOO WARM/COLD (YES = 1, NO = 0) |
| $V_{47}$ | Respondent-Q35-REASONS FOR SLEEP BEING DISTURBED-NOISE (YES = 1, NO = 0) |
| $V_{48}$ | Respondent-Q35-REASONS FOR SLEEP BEING DISTURBED-LIGHT (YES = 1, NO = 0) |
| $V_{49}$ | Respondent-Q35-REASONS FOR SLEEP BEING DISTURBED-SMELLS (YES = 1, NO = 0) |
| $V_{50}$ | Respondent-Q40-FREQUENCY TAKING VITAMIN SUPPLEMENTS (6 = EVERDAY) |
| $V_{51}$ | Respondent-Q44-NUMBER OF CAFFEINATED DRINKS CONSUMED EACH DAY (4 = MORE THAN 4 CUPS) |
| $V_{52}$ | Respondent-Q45-HOW HEALTHY DO YOU EAT (5 = EXTREMELY HEALTHY) |
| $V_{53}$ | Respondent-Q47-HOW STRESSFUL IS YOUR LIFE (5 = EXTREMELY STRESSFUL) |

TABLE 3

COEFFICIENTS AND CONSTANTS

| A | | B | | C | | D | | E | |
|---|---|---|---|---|---|---|---|---|---|
| $W_{A1}$ | −5.03481 | $W_{B1}$ | −3.32657 | $W_{C1}$ | −6.41283 | $W_{D1}$ | −1.9017 | $W_{E1}$ | −1.84041 |
| $W_{A2}$ | 2.86515 | $W_{B2}$ | 1.16363 | $W_{C2}$ | −1.39053 | $W_{D2}$ | 2.1262 | $W_{E2}$ | 4.40778 |
| $W_{A3}$ | 7.25343 | $W_{B3}$ | 4.91899 | $W_{C3}$ | 4.70919 | $W_{D3}$ | 4.97844 | $W_{E3}$ | 6.45077 |
| $W_{A4}$ | 0.77215 | $W_{B4}$ | 0.3698 | $W_{C4}$ | 0.44631 | $W_{D4}$ | 2.18927 | $W_{E4}$ | 3.21603 |
| $W_{A5}$ | −13.53785 | $W_{B5}$ | −9.49917 | $W_{C5}$ | −11.61919 | $W_{D5}$ | −14.47177 | $W_{E5}$ | −24.54775 |
| $W_{A6}$ | −6.26384 | $W_{B6}$ | −4.73265 | $W_{C6}$ | −1.0894 | $W_{D6}$ | −4.09167 | $W_{E6}$ | −14.96101 |
| $W_{A7}$ | 4.91627 | $W_{B7}$ | 2.28944 | $W_{C7}$ | 1.78096 | $W_{D7}$ | 5.3033 | $W_{E7}$ | 10.86091 |
| $W_{A8}$ | 9.60978 | $W_{B8}$ | 11.04179 | $W_{C8}$ | 12.78336 | $W_{D8}$ | 14.26397 | $W_{E8}$ | 22.76282 |
| $W_{A9}$ | 4.50266 | $W_{B9}$ | 4.24891 | $W_{C9}$ | 6.78872 | $W_{D9}$ | 2.71058 | $W_{E9}$ | 1.27952 |
| $W_{A10}$ | 5.79872 | $W_{B10}$ | 6.70748 | $W_{C10}$ | 6.90218 | $W_{D10}$ | 8.06332 | $W_{E10}$ | 6.77549 |
| $W_{A11}$ | 2.05002 | $W_{B11}$ | 2.81332 | $W_{C11}$ | 6.43626 | $W_{D11}$ | 7.87991 | $W_{E11}$ | 12.42265 |
| $W_{A12}$ | 7.13019 | $W_{B12}$ | 7.78881 | $W_{C12}$ | 7.78571 | $W_{D12}$ | 9.85302 | $W_{E12}$ | 7.37807 |
| $W_{A13}$ | 13.0662 | $W_{B13}$ | 10.91798 | $W_{C13}$ | 12.38146 | $W_{D13}$ | 10.65906 | $W_{E13}$ | 13.75115 |
| $W_{A14}$ | 5.84626 | $W_{B14}$ | 5.01957 | $W_{C14}$ | 2.84629 | $W_{D14}$ | 3.30128 | $W_{E14}$ | −4.00897 |
| $W_{A15}$ | 14.35454 | $W_{B15}$ | 13.74852 | $W_{C15}$ | 12.02993 | $W_{D15}$ | 12.9599 | $W_{E15}$ | 15.45324 |
| $W_{A16}$ | 3.16837 | $W_{B16}$ | 3.51648 | $W_{C16}$ | 3.20893 | $W_{D16}$ | 1.03277 | $W_{E16}$ | −0.70696 |
| $W_{A17}$ | 10.70804 | $W_{B17}$ | 10.83141 | $W_{C17}$ | 10.46987 | $W_{D17}$ | 9.37636 | $W_{E17}$ | 8.0314 |
| $W_{A18}$ | 78.28738 | $W_{B18}$ | 78.51756 | $W_{C18}$ | 79.8523 | $W_{D18}$ | 83.91855 | $W_{E18}$ | 93.36256 |
| $W_{A19}$ | 81.92217 | $W_{B19}$ | 87.84184 | $W_{C19}$ | 87.58114 | $W_{D19}$ | 87.2457 | $W_{E19}$ | 101.40503 |
| $W_{A20}$ | 78.63351 | $W_{B20}$ | 86.28866 | $W_{C20}$ | 86.93638 | $W_{D20}$ | 86.65417 | $W_{E20}$ | 102.20674 |

TABLE 3-continued

COEFFICIENTS AND CONSTANTS

| | A | | B | | C | | D | | E |
|---|---|---|---|---|---|---|---|---|---|
| $W_{A21}$ | 63.50097 | $W_{B21}$ | 68.59361 | $W_{C21}$ | 70.52393 | $W_{D21}$ | 69.55426 | $W_{E21}$ | 77.66964 |
| $W_{A22}$ | 3.44182 | $W_{B22}$ | 0.15277 | $W_{C22}$ | 5.69318 | $W_{D22}$ | −1.12491 | $W_{E22}$ | −4.40742 |
| $W_{A23}$ | 10.0591 | $W_{B23}$ | 9.82875 | $W_{C23}$ | 12.1122 | $W_{D23}$ | 7.59917 | $W_{E23}$ | 11.69212 |
| $W_{A24}$ | 11.71474 | $W_{B24}$ | 9.46744 | $W_{C24}$ | 16.06216 | $W_{D24}$ | 9.41853 | $W_{E24}$ | 8.32798 |
| $W_{A25}$ | −2.40053 | $W_{B25}$ | −0.5321 | $W_{C25}$ | −0.40143 | $W_{D25}$ | −0.08659 | $W_{E25}$ | 1.20704 |
| $W_{A26}$ | 3.42408 | $W_{B26}$ | 2.81038 | $W_{C26}$ | 5.34481 | $W_{D26}$ | 5.39178 | $W_{E26}$ | 9.99927 |
| $W_{A27}$ | 1.58022 | $W_{B27}$ | 6.32234 | $W_{C27}$ | 3.96203 | $W_{D27}$ | 3.04199 | $W_{E27}$ | −0.55476 |
| $W_{A28}$ | 8.87747 | $W_{B28}$ | 6.62846 | $W_{C28}$ | 1.36545 | $W_{D28}$ | 1.69279 | $W_{E28}$ | −1.59018 |
| $W_{A29}$ | 14.4482 | $W_{B29}$ | 15.59435 | $W_{C29}$ | 7.56485 | $W_{D29}$ | 15.52505 | $W_{E29}$ | 20.52038 |
| $W_{A30}$ | −6.32975 | $W_{B30}$ | −9.09096 | $W_{C30}$ | −5.6209 | $W_{D30}$ | −8.26135 | $W_{E30}$ | −10.52059 |
| $W_{A31}$ | −2.84589 | $W_{B31}$ | −4.68028 | $W_{C31}$ | −6.59683 | $W_{D31}$ | −2.50031 | $W_{E31}$ | −1.83753 |
| $W_{A32}$ | −6.29274 | $W_{B32}$ | −5.38067 | $W_{C32}$ | −1.85282 | $W_{D32}$ | −5.20866 | $W_{E32}$ | −8.16089 |
| $W_{A33}$ | 0.86533 | $W_{B33}$ | 0.21689 | $W_{C33}$ | 0.59462 | $W_{D33}$ | −0.1715 | $W_{E33}$ | 1.46984 |
| $W_{A34}$ | −1.00161 | $W_{B34}$ | 2.88752 | $W_{C34}$ | 3.17145 | $W_{D34}$ | 1.02958 | $W_{E34}$ | 2.17715 |
| $W_{A35}$ | 17.05898 | $W_{B35}$ | 17.2045 | $W_{C35}$ | 11.05842 | $W_{D35}$ | 16.88556 | $W_{E35}$ | 19.40689 |
| $W_{A36}$ | −10.75367 | $W_{B36}$ | −8.30602 | $W_{C36}$ | −8.61707 | $W_{D36}$ | −5.04753 | $W_{E36}$ | −8.40332 |
| $W_{A37}$ | 0.36254 | $W_{B37}$ | −3.49799 | $W_{C37}$ | −2.80702 | $W_{D37}$ | −1.18985 | $W_{E37}$ | −1.14465 |
| $W_{A38}$ | −19.32756 | $W_{B38}$ | −15.42999 | $W_{C38}$ | −16.92841 | $W_{D38}$ | −20.13988 | $W_{E38}$ | −32.79576 |
| $W_{A39}$ | 0.33108 | $W_{B39}$ | 0.28936 | $W_{C39}$ | 6.0703 | $W_{D39}$ | 3.56482 | $W_{E39}$ | 8.39871 |
| $W_{A40}$ | −0.50417 | $W_{B40}$ | −1.56768 | $W_{C40}$ | −1.52976 | $W_{D40}$ | −1.44652 | $W_{E40}$ | −1.43144 |
| $W_{A41}$ | 40.07422 | $W_{B41}$ | 34.64281 | $W_{C41}$ | 34.16851 | $W_{D41}$ | 38.45052 | $W_{E41}$ | 45.4052 |
| $W_{A42}$ | 12.50723 | $W_{B42}$ | 12.69321 | $W_{C42}$ | 12.30448 | $W_{D42}$ | 13.63575 | $W_{E42}$ | 15.64608 |
| $W_{A43}$ | −9.17133 | $W_{B43}$ | −6.97504 | $W_{C43}$ | −1.10747 | $W_{D43}$ | −3.99002 | $W_{E43}$ | −2.35332 |
| $W_{A44}$ | 0.24349 | $W_{B44}$ | −0.63206 | $W_{C44}$ | −0.78648 | $W_{D44}$ | 0.14629 | $W_{E44}$ | 3.93916 |
| $W_{A45}$ | −8.63626 | $W_{B45}$ | −5.86896 | $W_{C45}$ | −7.67355 | $W_{D45}$ | −4.62572 | $W_{E45}$ | −8.14927 |
| $W_{A46}$ | −3.71256 | $W_{B46}$ | −3.49322 | $W_{C46}$ | −1.32212 | $W_{D46}$ | −1.31128 | $W_{E46}$ | 2.40936 |
| $W_{A47}$ | 12.48024 | $W_{B47}$ | 10.77945 | $W_{C47}$ | 10.59542 | $W_{D47}$ | 11.26331 | $W_{E47}$ | 14.35998 |
| $W_{A48}$ | −8.06078 | $W_{B48}$ | −6.94508 | $W_{C48}$ | −7.48413 | $W_{D48}$ | −8.41228 | $W_{E48}$ | −10.89619 |
| $W_{A49}$ | −18.75243 | $W_{B49}$ | −18.41954 | $W_{C49}$ | −17.46166 | $W_{D49}$ | −17.98823 | $W_{E49}$ | −22.52914 |
| $W_{A50}$ | 1.51757 | $W_{B50}$ | 2.04889 | $W_{C50}$ | 1.62452 | $W_{D50}$ | 1.24405 | $W_{E50}$ | 0.77243 |
| $W_{A51}$ | 6.04014 | $W_{B51}$ | 6.03027 | $W_{C51}$ | 4.3963 | $W_{D51}$ | 5.5696 | $W_{E51}$ | 6.28266 |
| $W_{A52}$ | 2.80341 | $W_{B52}$ | 3.74745 | $W_{C52}$ | 3.70402 | $W_{D52}$ | 3.80916 | $W_{E52}$ | 4.06269 |
| $W_{A53}$ | 0.4751 | $W_{B53}$ | −1.04686 | $W_{C53}$ | −1.96563 | $W_{D53}$ | 0.80047 | $W_{E53}$ | 2.49099 |
| $C_A$ | −151.32817 | $C_B$ | −143.07719 | $C_C$ | −144.5403 | $C_D$ | −155.94759 | $C_E$ | −240.69533 |

The classification score $Y_A, Y_B, Y_C, Y_D$ and $Y_E$ outputted by each classification function represents the likelihood of a new user being classified by a TCM practitioner as having the specific skin composition A, B, C, D and E associated with the respective classification function. In other words, for each new user, each classification function will compute a classification score, and the skin composition associated with the classification function that renders the highest classification score is the skin composition of the user.

While the invention has been described in connection with a preferred embodiment, it is not intended to limit the scope of the invention to the particular form set forth but, on the contrary, it is intended to cover such alternatives, modifications, and equivalents as may be included within the spirit and scope of the invention as defined by the appended claims.

What we claim is:

1. A computer-aided diagnosis system for determining the skin composition of a specific user according to Traditional Chinese Medicinal (TCM) principles, said system comprising:

(1) a data entry module configured for entering into said system a clinical data set obtained from the specific user, wherein the clinical data set comprises biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user;

(2) a data processing module in communication with the data entry module, wherein said data processing module is configured for applying a statistical classification process to said clinical data set so as to classify the skin composition of the specific user according to TCM principles, wherein the statistical classification process comprises multiple classification functions, each of which is associated with a specific skin composition and is used to compute a classification score for a user representing the likelihood of said user being classified by a TCM practitioner as having the specific skin composition associated with the respective classification function, wherein the skin composition associated with the classification function that renders the highest classification score for the user is classified as the skin composition of the user, and wherein the classification functions are constructed by a discriminant analysis comprising:

(a) obtaining a training data set that comprises biological and/or psychological information of multiple users in a training sample selected from a population and classification of said users by a TCM practitioner with respect to their skin compositions according to TCM principles;

(b) identify a group of independent variables, each of which is representative of one type of biological and/or psychological information of the users in the training sample;

(c) calculating an F ratio for each one of the group of independent variables, which is indicative of the capability of said independent variable in discriminating between different groups of users of different skin compositions as determined by the TCM practitioner, wherein the F ratio for a specific independent variable is calculated as the ratio of between-group variance of said independent variable over the average within-group variance of said independent variable;

(d) selecting the independent variable with the largest F ratio;

(e) calculating F ratios for the remaining independent variables;

(f) repeating steps (d)-(e) until all independent variables having F ratios greater than a pre-set level of significance have been selected; and (g) using the selected independent variables to construct the multiple classification functions; and (3) an output module in communication with the data processing module and configured for displaying the skin composition of the specific user as determined by the data processing module.

2. The computer-aided diagnosis system of claim 1, wherein the skin composition classification of the specific user is indicative of Yin-Yang balance of the skin of the specific user or the lack thereof.

3. The computer-aided diagnosis system of claim 1, wherein the skin composition of the specific user is one of three different classifications or one of five different classifications.

4. The computer-aided diagnosis system of claim 1, wherein the data processing module is further configured for recommending one or more topical skin care regiments and/or ingestible skin benefit products suitable for the skin composition of the specific user.

5. The computer-aided diagnosis system of claim 1, wherein at least some of the biological and/or psychological information in the clinical data set is obtained through the specific user's self-evaluation as prompted by a questionnaire containing questions related to one or more topics selected from the group consisting of age, gender, bodily sensation, skin condition and complexion, sleep pattern, dietary habits, energy level, stress level, physical fitness, and emotional wellness of the specific user.

6. The computer-aided diagnostic system of claim 5, wherein the self-evaluation is conducted by the specific user remotely by filling out the questionnaire online.

7. The computer-aided diagnostic system of claim 5, wherein the self-evaluation is conducted by the specific user on site by filling out the questionnaire at a retail location.

8. The computer-aided diagnostic system of claim 5, wherein some of the biological and/or psychological information in the clinical data set is obtained through evaluation of the specific user by a trained holistic beauty specialist.

9. The computer-aided diagnostic system of claim 8, wherein the evaluation is conducted by the trained holistic beauty specialist through interactive consultation with the specific user.

10. The computer-aided diagnostic system of claim 8, wherein the evaluation is conducted on site by the trained holistic beauty specialist at a retail location.

11. The computer-aided diagnostic system of claim 5, wherein some of biological and/or psychological information in the clinical data set is obtained through measurements conducted on the specific user by an electronic device which measures one or more skin parameters.

12. The computer-aided diagnosis system of claim 1, wherein the statistical classification process employs a classification technique selected from the group consisting of discriminant analysis, logistic regression, naive Bayes classifier, support vector machines, quadratic classifiers, neural networks, perceptions, decision trees, Bayesian networks, hidden Markov models, and combinations thereof.

13. The computer-aided diagnosis system of claim 1, wherein the classification functions are either linear or quadratic.

14. The computer-aided diagnosis system of claim 1, wherein each classification function is a linear function having a general formula $C_x+W_{x1} \times V_1+W_{x2} \times V_2+ \ldots +W_{xm} \times V_m$, wherein $C_x$ is a constant associated with a specific skin composition, $V_1$ to $V_m$ are the selected independent variables, $W_{x1}$ to $W_{xm}$ are coefficients that each corresponds with one of the selected independent variables for the skin composition and are indicative of the relative weights of the selected variables in computing the classification score using the respective classification function.

15. The computer-aided diagnosis system of claim 1, wherein the classification functions are validated by using a validation data set that comprises biological and/or psychological information of multiple users in a validation sample and classification of said users by a TCM practitioner with respect to their skin compositions, and wherein said validation sample is selected from the same population as the training sample but contain a different group of users.

16. A computer-readable medium comprising code for determining the skin composition of a specific user according to Traditional Chinese Medicinal (TCM) principles, said code comprising instruction for applying a statistical classification process to a clinical data set obtained from the specific user so as to classify the skin composition of said specific user according to TCM principles, wherein said clinical data set comprises biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user, wherein the statistical classification process comprises multiple classification functions, each of which is associated with a specific skin composition and is used to compute a classification score for a user representing the likelihood of said user being classified by a TCM practitioner as having the specific skin composition associated with the respective classification function, wherein the skin composition associated with the classification function that renders the highest classification score for the user is classified as the skin composition of the user, and wherein each classification function is a linear function having a general formula $C_x+W_{x1} \times V_1+W_{x2} \times V_2+ \ldots +W_{xm} \times V_m$, wherein $C_x$ is a constant associated with a specific skin composition, $V_1$ to $V_m$ are selected independent variables that each represents one type of biological and/or psychological information of the user, $W_{x1}$ to $W_{xm}$ are coefficients each corresponding with one of the selected independent variables for the skin composition and are indicative of the relative weights of the selected independent variables in computing the classification score using the respective classification function.

17. The computer-readable medium of claim 16, wherein the skin composition classification of the specific user is indicative of Yin-Yang balance of the skin of the user or the lack thereof.

18. The computer-readable medium of claim 16, wherein the skin composition of the specific user is selected from one of three different classifications or one of five different classifications.

19. The computer-readable medium of claim 16, further comprising instruction for recommending one or more topical skin care regiments and/or ingestible skin benefit products suitable for the skin composition of the specific user.

20. A method for determining the skin composition of a specific user according to Traditional Chinese Medicinal (TCM) principles, comprising:
   (1) obtaining a clinical data set from the specific user, which comprises biological and/or psychological information selected from the group consisting of age, gender, bodily sensation, tongue color, tongue fur color, lip color, skin condition and complexion, sleep pattern, dietary habits, energy level, stress level, physical fitness and emotional wellness of the specific user;
   (2) applying a statistical classification process to said clinical data set of the specific user for classifying the skin composition of the specific user according to TCM principles,
   wherein the statistical classification process comprises multiple classification functions, each of which is associated with a specific skin composition and is used to compute a classification score for a user representing the likelihood of said user being classified by a TCM practitioner as having the specific skin composition associated with the respective classification function, wherein the skin composition associated with the classification function that renders the highest classification score for the user is classified as the skin composition of the user, and
   wherein the classification functions are constructed by a discriminant analysis comprising:
   (a) obtaining a training data set that comprises biological and/or psychological information of multiple users in a training sample selected from a population and classification of said users by a TCM practitioner with respect to their skin compositions according to TCM principles;
   (b) identifying a group of independent variables, each of which is representative of one type of biological and/or psychological information of the users in the training sample;
   (c) calculating an F ratio for each one of the group of independent variables, which is indicative of the capability of said independent variable in discriminating between different groups of users of different skin compositions as determined by the TCM practitioner, wherein the F ratio for a specific independent variable is calculated as the ratio of between-group variance of said independent variable over the average within-group variance of said independent variable;
   (d) selecting the independent variable with the largest F ratio;
   (e) calculating F ratios for the remaining independent variables;
   (f) repeating steps (d)-(e) until all independent variables having F ratios greater than a pre-set level of significance have been selected; and
   (g) using the selected independent variables to construct the multiple classification functions; and
   (3) outputting the skin composition of the specific user so determined.

21. The method of claim 20, wherein the skin composition classification of the specific user is indicative of Yin-Yang balance of the skin of the user or the lack thereof.

22. The method of claim 20, wherein the skin composition of the specific user is selected from one of three different classifications or one of five different classifications.

23. The method of claim 20, further comprising recommending one or more topical skin care regiments and/or ingestible skin benefit products suitable for the skin composition of the specific user.

24. The method of claim 20, wherein at least some of the biological and/or psychological information in the clinical data set is obtained through the specific user's self-evaluation as prompted by a questionnaire containing questions related to one or more topics selected from the group consisting of age, gender, bodily sensation, skin condition and complexion, sleep pattern, dietary habits, energy level, stress level, physical fitness, and emotional wellness of the specific user.

25. The method of claim 24, wherein the self-evaluation is conducted by the specific user remotely by filling out the questionnaire online.

26. The method of claim 24, wherein the self-evaluation is conducted by the specific user on site by filling out the questionnaire at a retail location.

27. The method of claim 24, wherein some of the biological and/or psychological information in the clinical data set is obtained through evaluation of the specific user by a trained holistic beauty specialist.

28. The method of claim 27, wherein the evaluation is conducted by the trained holistic beauty specialist through interactive consultation with the specific user.

29. The method of claim 27, wherein the evaluation is conducted on site by the trained holistic beauty specialist at a retail location.

30. The method of claim 24, wherein some of biological and/or psychological information in the clinical data set is obtained through measurements conducted on the specific user by an electronic device.

31. The method of claim 20, wherein the statistical classification process employs a classification technique selected from the group consisting of discriminant analysis, logistic regression, naive Bayes classifier, support vector machines, quadratic classifiers, neural networks, perceptrons, decision trees, Bayesian networks, hidden Markov models, and combinations thereof.

32. The method of claim 20, wherein the classification functions are either linear or quadratic.

33. The method of claim 20, wherein each classification function is a linear function having a general formula $C_x + W_{x1} \times V_1 + W_{x2} \times V_2 + \ldots + W_{xm} \times V_m$, wherein $C_x$ is a constant associated with a specific skin composition, $V_1$ to $V_m$, are the selected independent variables, $W_{x1}$ to $W_{xm}$ are coefficients that each corresponds with one of the selected independent variables for the skin composition and are indicative of the relative weights of the selected variables in computing the classification score using the respective classification function.

34. The method of claim 20, wherein the classification functions are validated by using a validation data set that comprises biological and/or psychological information of multiple users in a validation sample and classification of said users by a TCM practitioner with respect to their skin compositions, and wherein said validation sample is selected from the same population as the training sample but contain a different group of users.

* * * * *